US010368866B2

(12) United States Patent
Wang et al.

(10) Patent No.: US 10,368,866 B2
(45) Date of Patent: Aug. 6, 2019

(54) FLEXIBLE DRIVE MEMBER, END-EFFECTOR, AND SURGICAL INSTRUMENT USING THE SAME

(71) Applicant: REACH SURGICAL, INC., Tianjin (CN)

(72) Inventors: Yongfeng Wang, Tianjin (CN); Gan Zhang, Tianjin (CN)

(73) Assignee: Reach Surgical, Inc., Tianjin (CN)

( * ) Notice: Subject to any disclaimer, the term of this patent is extended or adjusted under 35 U.S.C. 154(b) by 541 days.

(21) Appl. No.: 15/190,369

(22) Filed: Jun. 23, 2016

(65) Prior Publication Data

US 2016/0296231 A1 Oct. 13, 2016

Related U.S. Application Data

(63) Continuation of application No. PCT/CN2014/088135, filed on Oct. 8, 2014.

(30) Foreign Application Priority Data

Dec. 27, 2013 (CN) .......................... 2013 1 0756202
Dec. 27, 2013 (CN) ...................... 2013 2 0895968 U

(51) Int. Cl.
*A61B 17/072* (2006.01)
*A61B 17/068* (2006.01)
(Continued)

(52) U.S. Cl.
CPC ...... *A61B 17/072* (2013.01); *A61B 17/00234* (2013.01); *A61B 17/068* (2013.01);
(Continued)

(58) Field of Classification Search
CPC ................ A61B 17/068; A61B 17/072; A61B 17/07207; A61B 17/115;
(Continued)

(56) References Cited

U.S. PATENT DOCUMENTS 4,646,745 A * 3/1987 Noiles .................. A61B 17/115
227/178.1
5,271,543 A * 12/1993 Grant ................... A61B 17/115
227/179.1
(Continued)

FOREIGN PATENT DOCUMENTS

CN 101156793 A 4/2008
CN 101224126 A 7/2008
(Continued)

OTHER PUBLICATIONS

International Search Report for PCT/CN2014/088135 dated Jan. 13, 2015.

*Primary Examiner* — Scott A Smith
(74) *Attorney, Agent, or Firm* — Arent Fox LLP; Michael Fainberg

(57) ABSTRACT

The disclosure relates to a surgical instrument and discloses a flexible drive member, an end-effector, and a surgical instrument. The flexible drive member includes a distal portion, a proximal portion, and a bendable portion therebetween, wherein the bendable portion includes a plurality of wire bundles extending in the length direction of the flexible drive member, and a flexible casing enclosing the plurality of wire bundles. In the technical solutions of the disclosure, the bendable portion is provided with some rigidity and flexibility due to the plurality of wire bundles, and the flexibly casing can fix the plurality of wire bundles relatively and can alleviate friction rate of the surface of the flexible drive member and further improve the rigidity of the flexible drive member.

16 Claims, 4 Drawing Sheets

(51) Int. Cl.
*A61B 17/00* (2006.01)
*A61B 17/29* (2006.01)

(52) U.S. Cl.
CPC .... *A61B 17/0686* (2013.01); *A61B 17/07207* (2013.01); *A61B 2017/00353* (2013.01); *A61B 2017/00424* (2013.01); *A61B 2017/07214* (2013.01); *A61B 2017/07271* (2013.01); *A61B 2017/07278* (2013.01); *A61B 2017/07285* (2013.01); *A61B 2017/2905* (2013.01); *A61B 2017/2927* (2013.01)

(58) Field of Classification Search
CPC .......... A61B 2017/07214; A61B 2017/07271; A61B 2017/07278
USPC .. 227/19, 175.1, 175.2, 176.1, 178.1, 180.1; 606/139, 153, 219
See application file for complete search history.

(56) References Cited

U.S. PATENT DOCUMENTS

| | | | | |
|---|---|---|---|---|
| 5,456,401 A | * | 10/1995 | Green | A61B 17/07207 227/176.1 |
| 5,485,952 A | * | 1/1996 | Fontayne | A61B 17/07207 227/111 |
| 5,849,011 A | * | 12/1998 | Jones | A61B 18/1477 606/47 |
| 5,868,760 A | * | 2/1999 | McGuckin, Jr. | A61B 17/00234 227/179.1 |
| 6,663,641 B1 | * | 12/2003 | Kovac | A61B 17/062 606/144 |
| 6,667,825 B2 | * | 12/2003 | Lu | C08G 61/02 359/265 |
| 6,786,382 B1 | * | 9/2004 | Hoffman | A61B 17/07207 227/175.1 |
| 6,877,647 B2 | * | 4/2005 | Green | A61B 17/07207 227/176.1 |
| 7,506,790 B2 | * | 3/2009 | Shelton, IV | A61B 17/07207 227/175.1 |
| 7,543,730 B1 | * | 6/2009 | Marczyk | A61B 17/07207 227/175.1 |
| 8,382,742 B2 | * | 2/2013 | Hermann | A61B 17/1631 606/1 |
| 8,469,254 B2 | * | 6/2013 | Czernik | A61B 17/07207 227/175.1 |
| 8,827,134 B2 | * | 9/2014 | Viola | A61B 17/07207 227/176.1 |
| 9,554,846 B2 | * | 1/2017 | Boudreaux | A61B 18/1445 |
| 2003/0045900 A1 | * | 3/2003 | Hahnen | A61B 17/07207 606/205 |
| 2005/0103819 A1 | * | 5/2005 | Racenet | A61B 17/07207 227/175.1 |
| 2006/0047308 A1 | * | 3/2006 | Ortiz | A61B 17/07207 606/219 |
| 2007/0175948 A1 | * | 8/2007 | Scirica | A61B 17/07207 227/175.1 |
| 2008/0083811 A1 | * | 4/2008 | Marczyk | A61B 17/07207 227/176.1 |
| 2008/0169329 A1 | * | 7/2008 | Shelton | A61B 17/105 227/180.1 |
| 2008/0223903 A1 | * | 9/2008 | Marczyk | A61B 17/072 227/175.1 |
| 2008/0308605 A1 | * | 12/2008 | Scirica | A61B 17/07207 227/175.1 |

FOREIGN PATENT DOCUMENTS

CN  102448388 A  5/2012
CN  203736252 U  7/2014

\* cited by examiner

FLEXIBLE DRIVE MEMBER, END-EFFECTOR, AND SURGICAL INSTRUMENT USING THE SAME

CROSS-REFERENCE TO RELATED APPLICATIONS

This application is a continuation of International Application No. PCT/CN2014/088135, filed on Oct. 8 2014, which claims priority to Chinese Patent Application No. 201310756202.4, filed on Dec. 27, 2013 and Chinese Patent Application No. 201320895968.6, filed on Dec. 27, 2013, all of which are hereby incorporated by reference in their entireties.

FIELD

The present disclosure relates to a surgical instrument and in particular to a flexible drive member, an end-effector, and a surgical instrument using the same.

BACKGROUND

A surgical stapling device is a surgical instrument widely applied to surgical procedures, which has functions of both cutting and stapling tissues. As illustrated in FIG. 1A, the surgical stapling device typically includes a handle 100, a longitudinal portion 200, and an end-effector 300, wherein the handle 100 is configured to be grasped and operated by an operator for controlling and actuating the device; the distal portion of the handle 100 is connected with the end-effector 300 through the longitudinal portion 200 (in the description that follows, the term "proximal" refers to the portion of the device closer to the operator and the term "distal" refers to the portion of the device further from the operator); the end-effector 300 is configured to be actuated and controlled by the handle 100 so as to cut and suture tissues. The end-effector may be designed as articulated or non-articulated. As illustrated in FIG. 1A and FIG. 1B, the articulating end-effector may comprise an anvil assembly 301 and a staple cartridge assembly 302, both of which may pivot around a pivotal axis 303 and be locked at an appropriate articulation angle.

The articulating end-effector is generally provided with a flexible drive member which may be bended along with pivotal movement of the anvil assembly and the staple cartridge assembly. As illustrated in FIG. 1C, the body of the flexible drive member 212 is formed through soldering multiple layers with each other; a proximal end 270 of the flexible drive member 212 is connected with a driving shaft (not shown), and a distal end 284 of the flexible drive member 212 is provided with a cutting surface 287, and a closure pin 286 together with a closure flange (not shown) adapted for closing the end-effector. In use, the end-effector is operated by the operator to articulate and open, so as to clamp tissues disposed between the anvil assembly and the staple cartridge assembly, and then a driving trigger is operated to force the driving shaft axially pushing the flexible drive member 212 to advance within the articulating end-effector; the closure pin 286 and the closure flange actuate the anvil portion and the staple cartridge portion of the end-effector to rotate towards each other for clamping the tissue, and subsequently the flexible drive member 212 drives a staple sled in the staple cartridge portion to further push a plurality of staple drivers, so that each of the staple driver further push each of staples out of the staple cartridge for firing, while the cutting surface 287 cuts the tissue clamped in the end-effector, to thereby accomplish cutting and stapling of the tissue.

Prior art may have problems, for example during assembling and using the flexible drive member, lack of solder at soldered joints is likely to occur between the layers, so that the layers may be warped and separated from one another, and the flexible drive member may fail to effectively transfer driving force due to its insufficient rigidity or may be permanently deformed and thus destroyed (that is when an elastomer is deformed under external force, it cannot return to its initial state even after the external force is released), which may hinder the driving stroke, and make it more difficult for a surgeon to operate; additionally, such a flexible drive member also may be complex to fabricate. The same problems occur in other similar surgical instruments having the flexible drive member.

SUMMARY

One of objectives of the present disclosure is to provide a flexible drive member, an end-effector, and a surgical instrument using the same, wherein the flexible drive member with preferred rigidity and flexibility can effectively transfer driving force and will not be easily permanently deformed and thus destroyed, thereby make it less difficult for a surgeon to operate, and also make it easier to be manufactured.

It is disclosed in one embodiment of the present disclosure a flexible drive member comprising a distal portion, a proximal portion, and a bendable portion disposed therebetween, wherein said bendable portion comprises a plurality of wire bundles extending in a length direction of said flexible drive member, and a flexible casing adapted for enclosing said plurality of wire bundles.

In the technical solutions according to the disclosure, the bendable portion is provided with certain rigidity and flexibility due to the plurality of wire bundles, and the flexibly casing can fix the plurality of wire bundles relatively and can alleviate a friction force on the surface of the flexible drive member and further improve the rigidity of the flexible drive member. The flexible drive member can effectively transfer driving force for the instrument, and will not be easily permanently deformed and thus destroyed during articulating, firing and retracting, to thereby make it less difficult for a surgeon to operate, and also make it easier to be manufactured because of omitted soldering step.

Preferably each of said plurality of wire bundles comprises at least one metal filament.

Preferably said metal filament is made of nitinol shape memory material.

Optionally the plurality of wire bundles are knitted to form a ribbon.

Optionally said plurality of wire bundles are arranged so as to form at least one layer, and two adjacent filaments of said plurality of wire bundles in a same layer are arranged densely or spaced apart from each other.

Both of the embodiments above can provide the bendable portion, with desirable rigidity and flexibility, and enable the flexible drive member to be easily fabricated at a low cost.

When the plurality of wire bundles are arranged in at least one layer, optionally said plurality of wire bundles are arranged in any one pattern of straight line, zigzag or curve, and/or each of said plurality of wire bundles is formed through said filaments being wound helically. The pattern of the plurality of wire bundles may be changed to thereby change the flexibility of the bendable portion, so an appropriate pattern may be selected for a particular material property of the wires to provide the bendable portion with preferred rigidity and flexibility.

Preferably at least one transmission cable is arranged among said plurality of wire bundles, or a transmission cable is arranged among filaments of at least one of said plurality of wire bundles; said transmission cable is an electrical cable or an optical fiber. A control signal or a video signal may be transmitted over the transmission cable to thereby facilitate provision of a number of control functions of the surgical instrument so as to improve the precision in operation.

Optionally said flexible casing is formed upon said plurality of wire bundles in an injection molding manner or in an extrusion molding manner. The flexible casing can be easily fabricated and molded with high reliability, and is enabled to fix the plurality of wire bundles reliably.

Optionally said flexible casing is made of transparent nylon material.

Optionally said flexible casing is soldered, riveted or over-engaged with said distal portion and/or said proximal portion, all of which can achieve reliable connection between the components.

Preferably said distal portion comprises a first pair of hooks, said proximal portion comprises a pair second of hooks, and said bendable portion comprises a third pair of hooks over-engaged with said first pair of hooks and a fourth pair of hooks over-engaged with said second pair of hooks, respectively.

Optionally said flexible casing is integrally formed with said distal portion and/or said proximal portion. This solution can further simplify fabrication and assembly processes of the flexible drive member.

It is further disclosed in one embodiment of the present disclosure an end-effector including the flexible drive member according to any one of the technical solutions above. The flexible drive member in the end-effector can effectively transfer driving force for the instrument, will not be easily permanently deformed and thus destroyed, and can enable a precise drive stroke to thereby make it less difficult for the surgeon to operate.

It is further disclosed in one embodiment of the present disclosure a surgical instrument including the end-effector according to the technical solution above. The flexible drive member in the end-effector can effectively transfer driving force for the instrument and will not be easily permanently deformed and thus destroyed to thereby provide the instrument with preferred precision in operation and reliability in use.

BRIEF DESCRIPTION OF THE DRAWINGS

Various embodiments of the present disclosure are disclosed herein with reference to the drawings, wherein.

Figure 1A:
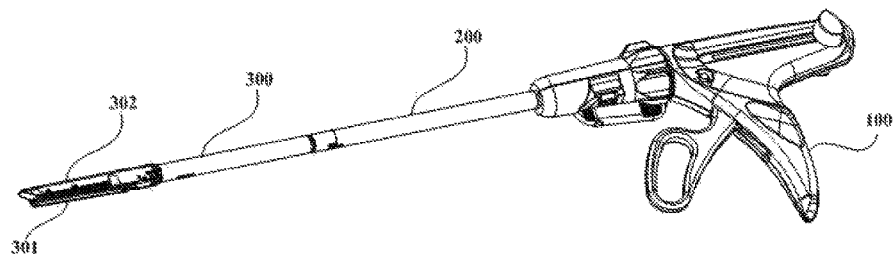
FIG. 1A illustrates a schematic diagram of a general structure of the surgical stapling device.
Figure 1B:
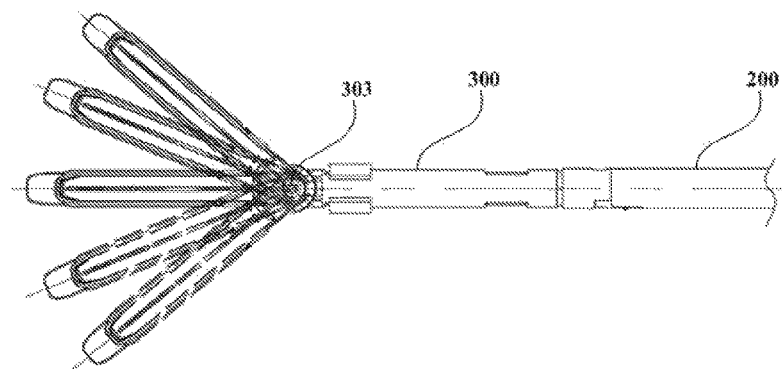
FIG. 1B shows the pivotal movement of the end-effector of one embodiment of the present disclosure.
Figure 1C:
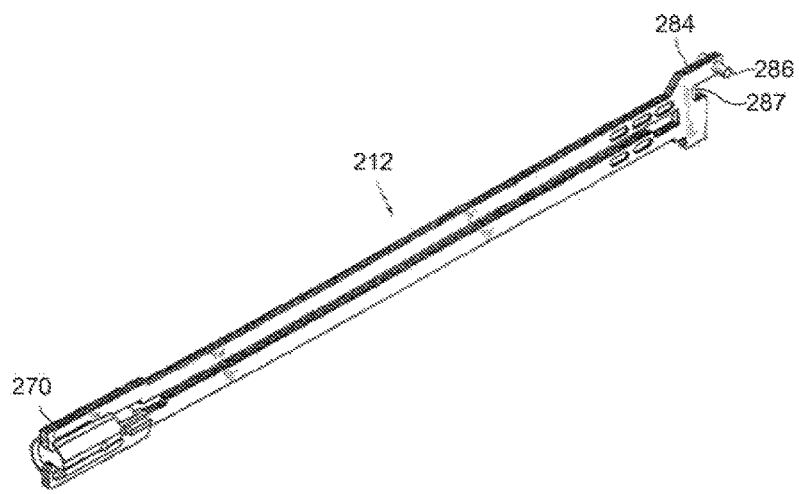
FIG. 1C illustrates a schematic structural diagram of the flexible drive member of prior art.

In the drawings, the following reference numbers are used:

100—handle; 200—longitudinal portion; 300—end-effector; 301—anvil assembly; 302—staple cartridge assembly; 303—pivotal axis; 212—flexible drive member; 270—proximal end; 284—distal end; 287—cutting surface; 286—closure pin; 210—articulation rod; 1—distal portion; 2—proximal portion; 3—bendable portion; 4—wire bundle; 40—filament; 5—flexible casing; 6—transmsison cable; 7—first pair of hooks; 8—second pair of hooks; 9—third pair of hooks; 10—fourth hook.

DETAILED DESCRIPTION OF THE EMBODIMENTS

In order to effectively transfer driving force for a surgical instrument and to alleviate a flexible drive member of the surgical instrument from being permanently deformed so as to make it less difficult for a surgeon to operate, it is provided in one embodiment of the disclosure a flexible drive member, an end-effector, and a surgical instrument using the same. It is disclosed in one embodiment that the flexible drive member comprises a bendable portion including a plurality of wire bundles extending in the length direction of the flexible drive member, and a flexible casing arranged for enclosing the plurality of wire bundles. The bendable portion may have certain rigidity and flexibility due to the plurality of wire bundles, and the flexibly casing can fix the plurality of wire bundles with respect to each other and can alleviate friction rate of the surface of the flexible drive member and further improve the rigidity of the flexible drive member. The flexible drive member can effectively transfer driving force for the instrument, and will not easily be permanently deformed during articulating, firing and retracting, to thereby make it less difficult for the surgeon to operate the surgical instrument, and also make it easier to fabricate the flexible drive member due to lack of soldering process. In order to clearly describe the objectives, technical solutions and advantages of the disclosure, the detailed embodiments of the present disclosure are disclosed herein.

Figure 2A:
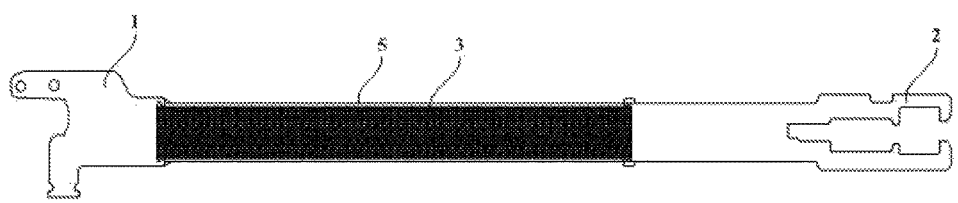
FIG. 2A illustrates a schematic structural diagram of a flexible drive member according to one embodiment of the disclosure.
Figure 2B:
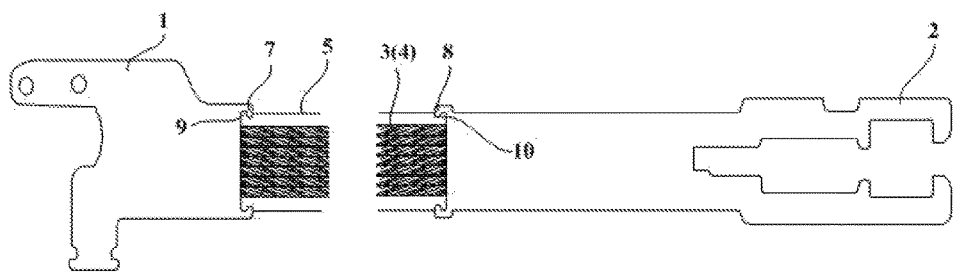
FIG. 2B illustrates a schematic diagram of details in assembling in the embodiment illustrated in FIG. 2A.

Referring to FIG. 2A and FIG. 2B, it is disclosed in one embodiment of the present disclosure that the flexible drive member comprises a distal portion 1, a proximal portion 2, and a bendable portion 3 arranged therebetween, wherein the bendable portion 3 comprises a plurality of wire bundles 4 extending longitudinally, and a flexible casing 5 arranged for enclosing the plurality of wire bundles 4.

Figure 2C:
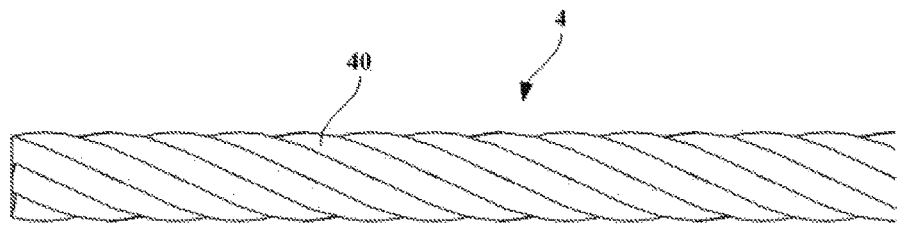
FIG. 2C illustrates a schematic structural diagram of metal filaments of wire bundles.

In one embodiment of the present disclosure, the distal portion 1 may be provided with a knife having a cutting surface and a closure mechanism configured to close the end-effector (such as an I-beam, an E-beam, or a "back-to-back Es" beam etc.), and the proximal portion 2 may be engaged with a driving shaft. As illustrated in FIG. 2C, each wire bundle 4 is formed through a plurality of filaments 40 being wound helically. It is preferred that the filament 40 has a certain flexibility and rigidity, for example, the filament 40 may be metal filament, for example, steel filament, filament for spring, etc, or non-metal fiber. It should be noted that there is no limitation here on the cross section of the filament 40, which may be, for example, round, ellipse, polygon (such as triangle, square, etc.), and so on. Preferably the metal filament is made of nitinol shape memory material that has some properties such as shape-memory and super elasticity, thus it may recover its initial shape rapidly after being released. The filament made of nitinol shape memory material could not be soldered to another metal due to its property, so it is disclosed in one embodiment of the present disclosure that the filaments made of nitinol shape memory material can be attached to the proximal portion and/or distal portion of the flexible drive member which are/is made of metal, using transparent nylon material in injection molding manner. For ensuring reliability of attachment, the distal portion 1 and/or the proximal portion 2 of the flexible drive member may be provided with reserved holes, dovetail grooves, back taper, trapezoids and/or other connection fixing structures for injection molding.

In one embodiment of the disclosure, it is preferred that the flexible casing 5 is formed upon the surface of the plurality of wire bundles 4 in an injection molding manner or in an extrusion molding manner, which is a simple and reliable process; and the flexible casing 5 is plastically coupled with the plurality of wire bundles 4 so as to reliably enclose the plurality of wire bundles 4. In an alternative embodiment of the disclosure, the flexible casing 5 may alternatively be formed in an injection molding manner or an extruding molding manner and then be assembled together with the plurality of wire bundles 4. It is preferred that the flexible casing 5 is made of transparent nylon material. Thus, the filaments made of nitinol shape memory material can be attached to the proximal portion and/or the distal portion of the flexible drive member using transparent nylon material in injection molding manner, more specifically, the filaments made of nitinol shape memory material can be enclosed through the flexible casing 5 made of nylon, so that the filaments can be attached to the metal portion(s) of the flexible drive member, which would be the proximal portion and/or the distal portion thereof.

It is disclosed in one embodiment of the present disclosure that the wire bundles 4 may be knitted into a ribbon or may be so arranged to form a single or multiple layers. When the bundles 4 are arranged in a single or multiple layers, each two adjacent bundles 4 may be arranged densely (shown in FIG. 2D) or spaced apart from each other (shown in FIG. 2E) and further be enclosed by the flexible casing 5. The pattern into which the wire bundles 4 are knitted or arranged can be verified so that the bendable portion 3 can be provided with desirable rigidity and flexibility, thus making it convenient to be manufactured the bendable portion 3, at a low cost.

In one embodiment of the present disclosure, the bendable portion 3 has a certain rigidity and flexibility due to the plurality of wire bundles 4, and the flexible casing 5 can fix the plurality of wire bundles 4 and reduce friction force on the surface of the flexible drive member, and it may also increase rigidity of the flexible drive member. Therefore, the flexible drive member can effectively transfer driving force for the instrument, and will not be easily permanently deformed during articulating, firing and retracting, which thereby may facilitate surgeons to perform surgeries, and also simplify the process for manufacturing the flexible drive member because of omitted welding step.

When the plurality of the wire bundles 4 are arranged in at least one layer, each of the wire bundles 4 can be arranged in any one pattern of straight line, zigzag or curve. FIG. 2B illustrates the wire bundles 4 in pattern of straight line. Changing the pattern of the wire bundles 4 may thereby change flexibility of the bendable portion 3 (for example, flexibility of the wire bundles in pattern of straight line is higher than that of those in pattern of zigzag or curve). So based on different filaments of the wire bundles with different properties, the bundles may be designed in different pattern accordingly, so as to provide the bendable portion 3 with preferred rigidity and flexibility.

Figure 2D:
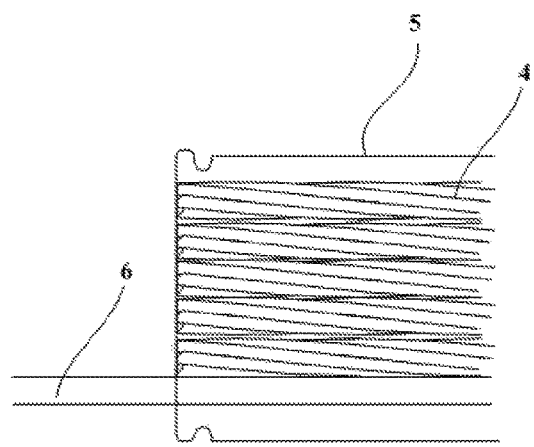
FIG. 2D illustrates a schematic diagram of a partial structure of a bendable portion, where the metal wire bundles are arranged densely.
Figure 2E:
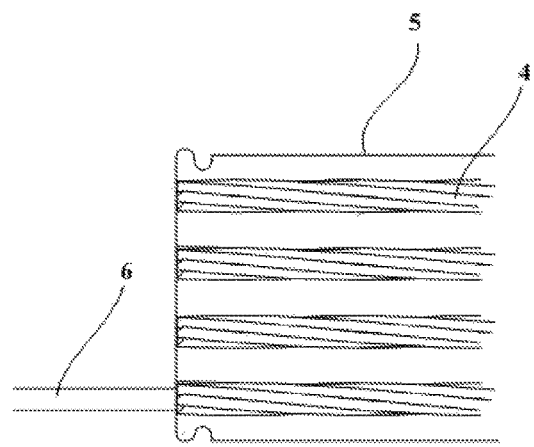
FIG. 2E illustrates a schematic diagram of a partial structure of the bendable portion, where the metal wire bundles are arranged spaced apart from each other.

Preferably, at least one transmission cable is arranged among the plurality of wire bundles, or at least one transmission cable is arranged among filaments of at least one of the plurality of wire bundles. Referring to FIG. 2E, the flexible drive member further includes a transmission cable 6 (including a core and a casing) interposed among the filaments 40 of any one of the wire bundles 4, where the transmission cable 6 can be an electrical cable or an optical fiber cable. Alternatively, the transmission cable 6 can be arranged among the plurality of wire bundles, for example, the transmission cable 6 can be arranged parallel with the wire bundles 4 (as illustrated in FIG. 2D) or be knitted together with the filaments 40 so as to form a wire bundle 4.

Electric signal may be transmitted through the electrical cable, and optical signal may be transmitted through the optical fiber cable. For expanding functions of surgical instruments and improving precision of operating surgeries, the transmission cable 6 may be utilized to transmit control signal or video signal. For example, the transmission cable 6 can be utilized to transmit video signal to thereby monitor operations of the end-effector. The transmission cable 6 can be arranged among the filaments 40 of anyone of the wire bundles 4 in any appropriate position, e.g., in the center of any one of the wire bundles 4 which is coaxial therewith, or being wound together with the filaments 40 of any one of the wire bundles 4.

The flexible casing 5 can be soldered, riveted or over-engaged with the distal portion 1 and/or the proximal portion 2 to thereby achieve reliable connection therebetween. As illustrated in FIG. 2B, the distal portion 1 includes a first pair of hooks 7, the proximal portion 2 includes a second pair of hooks 8, and the bendable portion 3 includes a third pair of hooks 9 over-engaged with the first pair of hooks 7, and a fourth pair of hooks 10 over-engaged with the second pair of hooks 8. The first pair of hooks 7, the second pair of hooks 8, the third pair of hooks 9, and the fourth pair of hooks 10 can be formed through punching.

Figure 3:
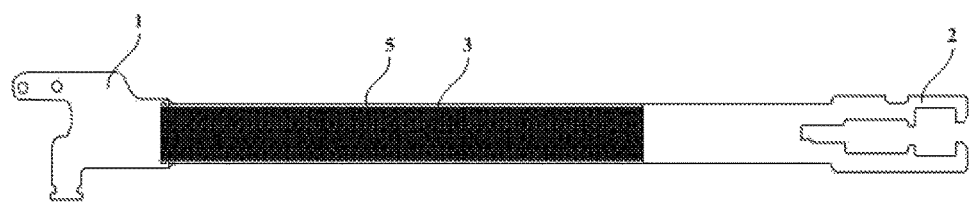
FIG. 3 illustrates a schematic structural diagram of a flexible drive member according to another embodiment of the disclosure.

Additionally the flexible casing 5 can alternatively be integral formed with the distal portion 1 or the proximal portion 2, or the flexible casing 5 can alternatively be integral formed with both the distal portion 1 and the proximal portion 2, in an injection molding manner or an extruding molding manner, which may simplify the processes and assembling steps. FIG. 3 shows one embodiment where the flexible casing 5 is integral formed with the proximal portion 2.

Figure 4A:
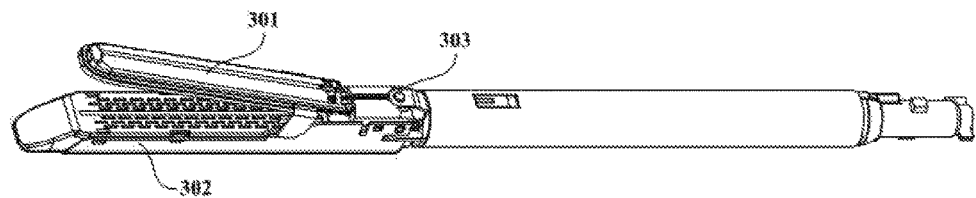
FIG. 4A illustrates a schematic structural diagram of an end-effector according to an embodiment of the disclosure.
Figure 4B:
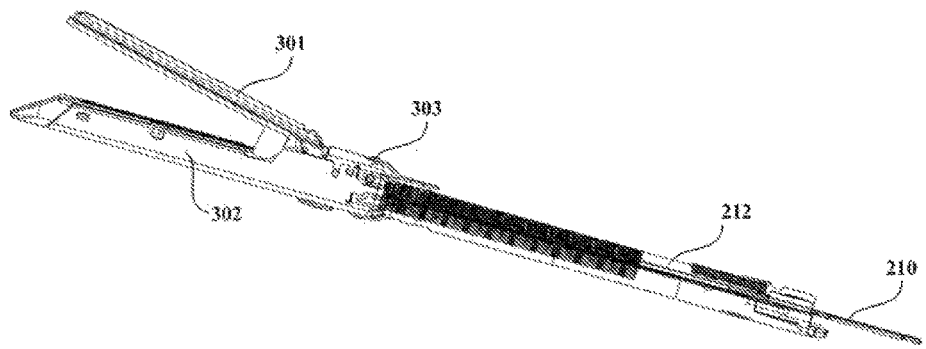
FIG. 4B illustrates a schematic diagram of an internal structure of an end-effector according to an embodiment of the disclosure.

Referring to FIG. 4A and FIG. 4B, it is provided in one embodiment of the disclosure an end-effector includes the flexible drive member 212 of any one of the above mentioned embodiments. The end-effector comprises an anvil portion 301 and a staple cartridge portion 302 pivotally engaged therewith. The end-effector further comprises an articulation rod 210, through which the anvil portion 301 and the staple cartridge portion 302 can rotate about the pivotal axis 303, so as to articulate the end-effector. The driving trigger is operated to force the driving shaft axially pushing the flexible drive member 212 to advance within the articulating end-effector, to thereby close the articulating end-effector, and to cut and staple the tissue. The flexible drive member 212 in the end-effector can effectively transfer driving force for the instrument, will not be easily permanently deformed and thus destroyed, and can enable a precise drive stroke to thereby make it less difficult for the surgeon to operate the surgical instrument.

It shall be noted that the end-effector will not be limited to an end-effector with the cutting and stapling functions, but the flexible drive member according to any one of the embodiments of the disclosure can be applied to any end-effector as long as the end-effector is of the articulating type and is required to be driven by the flexible drive member, e.g., an articulating end-effector only with the cutting function or only with the stapling function, etc.

It is disclosed in one embodiment of the present disclosure that a surgical instrument comprises a handle portion, an elongated body portion extending distally from the handle portion, and an end-effector mounted on a distal end of the elongated body portion which is provided with a flexible drive member of any one of the above mentioned embodiments. The flexible drive member of the surgical instrument can effectively transfer driving force for the surgical instrument and will not be easily permanently deformed and thus destroyed to thereby provide the instrument with preferred precision in operation and reliability in use.

Evidently those skilled in the art can make various modifications and variations to the disclosure without departing from the spirit and scope of the disclosure. Thus the disclosure is also intended to encompass these modifications and variations thereto so long as the modifications and variations come into the scope of the claims appended to the disclosure and their equivalents.

We claim:

1. A flexible drive member comprising a distal portion, a proximal portion, and a bendable portion disposed therebetween, wherein,
   said bendable portion comprises a plurality of wire bundles extending in a length direction of said flexible drive member, and a flexible casing adapted for enclosing said plurality of wire bundles;
   wherein each of said plurality of wire bundles comprises at least one metal filament, and said metal filament is made of nitinol shape memory material.

2. The flexible drive member according to claim 1, wherein said plurality of wire bundles are knitted to form a ribbon.

3. The flexible drive member according to claim 1, wherein said plurality of wire bundles are arranged to form at least one layer, and two adjacent wire bundles in a same layer are arranged densely with respect to each other.

4. The flexible drive member according to claim 1, wherein said flexible casing is formed upon said plurality of wire bundles in an injection molding manner.

5. The flexible drive member according to claim 1, wherein said flexible casing is made of transparent nylon material.

6. The flexible drive member according to claim 1, wherein said distal portion comprises a first pair of hooks, said proximal portion comprises a second pair of hooks, and said bendable portion comprises a third pair of hooks over-engaged with said first pair of hooks and a fourth pair of hooks over-engaged with said second pair of hooks, respectively.

7. The flexible drive member according to claim 1, wherein said flexible casing is integrally formed with at least one of said distal portion and said proximal portion of said driving member.

8. The flexible drive member according to claim 1, wherein said plurality of wire bundles are arranged to form at least one layer, and two adjacent wire bundles in a same layer are spaced apart from each other.

9. The flexible drive member according to claim 1, wherein said flexible casing is formed upon said plurality of wire bundles in an extrusion molding manner.

10. An end-effector, comprising a flexible drive member provided with a distal portion, a proximal portion, and a bendable portion disposed therebetween, wherein,
    said bendable portion comprises a plurality of wire bundles extending in a length direction of said flexible drive member, and a flexible casing adapted for enclosing said plurality of wire bundles;
    wherein each of said plurality of wire bundles comprises at least one metal filament, and said metal filament is made of nitinol shape memory material.

11. The end-effector according to claim 10, wherein said end-effector further comprises an anvil portion and a staple cartridge portion pivotally engaged therewith; and an articulation rod, through which said anvil portion and said staple cartridge portion can rotate about an pivotal axis.

12. A surgical instrument, comprising:
    a handle portion;
    an elongated body portion extending distally from the handle portion;
    an end-effector mounted on a distal end of the elongated body portion, wherein said end effector comprises a flexible drive member provided with a distal portion, a proximal portion, and a bendable portion disposed therebetween, wherein,
    said bendable portion comprises a plurality of wire bundles extending in a length direction of said flexible drive member, and a flexible casing adapted for enclosing said plurality of wire bundles;
    wherein each of said plurality of wire bundles comprises at least one metal filament, and said metal filament is made of nitinol shape memory material.

13. The surgical instrument according to claim 12, wherein said end-effector further comprises an anvil portion and a staple cartridge portion pivotally engaged therewith; and an articulation rod, through which said anvil portion and said staple cartridge portion can rotate about an pivotal axis.

14. The surgical instrument according to claim 12, wherein said plurality of wire bundles are knitted to form a ribbon.

15. The surgical instrument according to claim 12, wherein said plurality of wire bundles are arranged to form at least one layer, and two adjacent wire bundles in a same layer are arranged densely with respect to each other.

16. The surgical instrument according to claim 12, wherein said plurality of wire bundles are arranged to form at least one layer, and two adjacent wire bundles in a same layer are spaced apart from each other.

* * * * *